United States Patent
Anastasie

(10) Patent No.: US 8,454,586 B2
(45) Date of Patent: Jun. 4, 2013

(54) LASER INSTRUMENT FOR VASCULAR OCCLUSION, IN PARTICULAR FOR INTRAVENOUS TREATMENT, AND FOR PERFORATION OR DETERSION OF TISSUE

(76) Inventor: Bruno Anastasie, La Varenne-Saint-Hilaire (FR)

(*) Notice: Subject to any disclaimer, the term of this patent is extended or adjusted under 35 U.S.C. 154(b) by 860 days.

(21) Appl. No.: 12/282,401

(22) PCT Filed: Mar. 13, 2006

(86) PCT No.: PCT/FR2006/000546
§ 371 (c)(1),
(2), (4) Date: Nov. 24, 2009

(87) PCT Pub. No.: WO2007/104836
PCT Pub. Date: Sep. 20, 2007

(65) Prior Publication Data
US 2010/0063493 A1    Mar. 11, 2010

(51) Int. Cl.
*A61B 18/18* (2006.01)
*A61B 18/24* (2006.01)
*A61B 18/22* (2006.01)

(52) U.S. Cl.
CPC *A61B 18/24* (2013.01); *A61B 18/22* (2013.01)
USPC .............................................. 606/15; 606/17

(58) Field of Classification Search
CPC ................................. A61B 18/24; A61B 18/22
USPC ..................... 606/1, 2, 13–15, 17; 607/88, 89
See application file for complete search history.

(56) References Cited

U.S. PATENT DOCUMENTS

| 2003/0199860 | A1 | 10/2003 | Loeb |
| 2005/0131399 | A1* | 6/2005 | Loeb et al. ....................... 606/15 |
| 2005/0131400 | A1 | 6/2005 | Hennings |

FOREIGN PATENT DOCUMENTS

| EP | 1350481 | 10/2003 |
| ES | 2188398 | 6/2003 |
| WO | 9824513 | 6/1998 |
| WO | 0103596 | 1/2001 |

\* cited by examiner

*Primary Examiner* — Huy K Mai
(74) *Attorney, Agent, or Firm* — Lowe Hauptman Ham & Berner, LLP

(57) ABSTRACT

An instrument comprises a light guide and a substantially rigid support for the light guide. In a version adapted for the treatment of varicose veins, the support is a needle serving as a sheath to a fibre optic.

14 Claims, 2 Drawing Sheets

LASER INSTRUMENT FOR VASCULAR OCCLUSION, IN PARTICULAR FOR INTRAVENOUS TREATMENT, AND FOR PERFORATION OR DETERSION OF TISSUE

RELATED APPLICATION

The present application is based on, and claims priority from, PCT Application Number PCT/FR06/000546, filed Mar. 13, 2006, the disclosure of which is hereby incorporated by reference herein in its entirety.

FIELD OF THE INVENTION

This present invention relates to an instrument for treatment by light, and in particular to an endoveinous laser capable of being used for the treatment of varices.

BACKGROUND OF THE INVENTION

Phlebectomy is a difficult and costly surgical operation. It also leaves scars.

More recent techniques employed for vascular sclerosis, in particular the treatment of varices, such as the technique presented in document US 2003/0078569, although they are less traumatic for the patient, nevertheless necessitate preparation for catheterisation, covering of the operator, sterile conditions, thorough disinfecting, and complex procedures. They also employ long and costly optical fibres. In addition, this technique requires the injection of a substance that is liable to give rise to allergies. This is the case with conventional sclerosis in the doctors surgery that make use of chemical sclerosants.

SUMMARY OF THE INVENTION

The aim of the invention is to propose a simpler technique, with equipment, instruments and systems that are less costly and easier to manipulate.

According to a first objective of the invention, such an instrument includes a light guide, such as an optical fibre, and a rigid support for the guide, like a needle forming a sheath around the light guide.

Such an optical needle would be connected to a laser source of variable wavelength by a light vector connected at either end to the laser and to the needle by a standard connector (SMA or other), capable of chemical sterilisation for use in a sterile surgical environment. Thus, in contrast to previous uses in which the flexibility of an optical fibre is favoured, in order for example to be able to pass through a vein or even an artery over a large distance from the insertion of the fibre up to a zone to be treated, here on the other hand, we favour a certain rigidity that is afforded by the support. Of course this rigidity is not absolute, but is rather comparable to the flexibility of an optical fibre as used in the endoveinous laser in particular. This rigidity can be nuanced according to the use concerned. For example in the case of a bevelled needle, the latter can be sufficiently rigid to allow insertion through the skin of a patient.

Preferably, for the treatment of varices, the needle can have an outside diameter falling in a range between 0.45 mm and 1 mm. The light guide can have an outside diameter of 200 to 1000 microns (1 mm).

The instrument can advantageously include means for connection to a light source, in particular to a laser light source. The laser light source can have a wavelength of between 800 and 980 nm, which is suitable for endovascular use. Other wavelengths can equally well be employed, according to the application concerned. The needle can be straight or curved. The length of the needle and of the light guide can vary according to the application involved.

The light guide can include an inner lining of a tubular needle for example. This coating can advantageously take the form of silica.

As a variant, the instrument can include an optical fibre as a light guide, such as a fibre of a type currently used for medical applications. This fibre can be mounted in a tubular needle.

The instrument can include means for a substantially frontal emission of the light and/or for a lateral emission of the light. The lateral diffusion can be achieved through one or more lateral windows. According to the use concerned, the windows can be distributed transversally or longitudinally along the light guide and/or the support.

The instrument can also include a channel, with the reflux of blood in the channel attesting to the correct intravascular position of the needle. A channel can also be provided in order to inject an anaesthetic.

According to a second objective of the invention, a treatment system can also include a laser light source. In particular for the treatment of varices, the wavelength of this light is advantageously between 800 and 1000 nm. Yet more advantageously, this wavelength is 980 nm, because of its favoured absorption by oxygenated haemoglobin and by water.

According to a third objective of the invention, a method of treatment by light laser can advantageously employ an instrument or a system according to the invention. In particular, it can be used for vascular applications, in particular for the treatment of varices. For treating the latter, the laser can be used for the sclerosis of the varix. It can also be used for arterial occlusion, then replacing chemical embolisation.

After local anaesthesia for example, the instrument of the invention is inserted at the position of a varix to be treated, through the skin, just as for a puncture. The injection can be achieved under sight control or under ultrasound control. The instrument can itself be used to injection of an anaesthetic through a channel provided for this purpose, thus avoiding an injection and the use of an additional syringe. A channel, possibly the same, can also be provided to verify the inflow of blood. It is thus possible to verify the correct positioning of the instrument in the vascular system. Anaesthesia is effected by perivascular intumescence. Location can be achieved using ultrasound.

When the instrument is in position, a laser pulse is then fired. It is advantageous to effect a rotation at the end of the light guide in order to effect circumferential lesion of the wall of the varix to be treated. One thus achieves a sclerosis of the varix, which is then no longer irrigated. In endoveinous laser treatment, one observes a photocoagulation of the blood with tissular retraction by contraction of the collagen in a greater proportion in the varicose vein.

The instrument is then withdrawn, and can be decarbonised with a sterile compress. The instrument is then ready to treat another varix. A direct puncture without the guide needle is also possible.

The optical fibre used can be a fibre of any usual type, in particular of a type used for surgical fibroscopy, endoveinous laser treatment, surgery, etc.

The cost of an instrument according to the invention can be divided by five or ten in relation to an instrument used currently for the treatment of varices by light laser, if it is manufactured on a large scale.

Other particular features and advantages of the invention will emerge from the description that follows, relating to examples that are not limiting.

DETAILED DESCRIPTION OF THE DRAWING

In what follows, the word needle refers to a needle of the tubular type that is sufficiently rigid to allow precise manipulation of the light guide. Also, in particular for endoveinous treatments, this needle must be sufficiently rigid to pierce the skin, as would a puncture needle.

Figure 1:
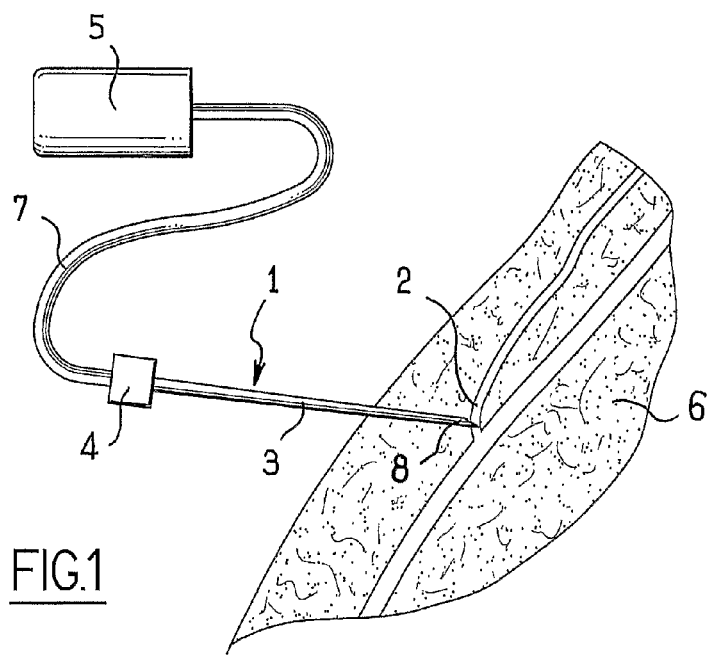
FIG. 1 is a schematic view of a system according to a preferred embodiment of the invention, in the process of being used.

FIG. 1 very schematically illustrates the use of a, instrument (1) according to a preferred embodiment of the invention for the treatment of a varix (2). The instrument takes the form of a needle (3) containing a guide for a light laser. The contact of the guide with the end-piece of the needle can be of conical shape in order that the guide will fit in a consistent manner. The instrument includes connection means (4) for a laser light source (5). An optical cable (7) links the laser source (5) and the connection means (4). In the position illustrated, the needle (3) has been inserted into a lower limb (6). A distal end (8) of the needle, that is its end furthest away from the light source (5), is inserted into one end of the varix (2). A laser pulse can then be administered through the distal end (8) of the needle in order to provoke sclerosis of the end of the varix, and then prevent the inflow of blood into the varix. Several laser pulses can be administered along the varix treated, about every 2 mm, while withdrawing the needle progressively. Markings can be arranged on the sheath of the needle.

Figure 2:
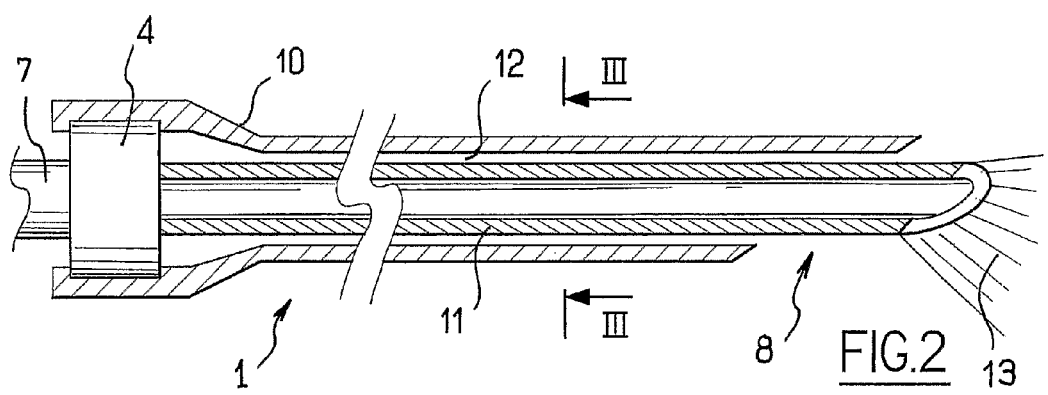
FIG. 2 is a view in longitudinal section of a first embodiment of a needle with an optical guide in the form of an optical fibre and in which diffusion of the light is effected through an axial opening.
Figure 3:
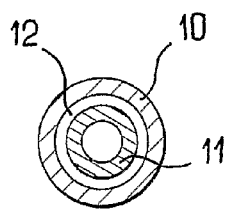
FIG. 3 is a cross section along III-III of the needle of FIG. 2.

FIGS. 2 and 3 are illustrations of a first embodiment of an instrument (1) according to the preferred embodiment of the invention. In this first embodiment, the instrument includes a tubular needle (10). The needle (10) is bevelled at distal end (8) of the instrument (1). The instrument also includes an optical fibre (11), also bevelled at distal end (8). The needle (10) forms a tubular sheath for the optical fibre (11). At the distal end (8) of the instrument (1), the bevelled distal end (81) of the optical fibre (11) extends beyond the bevelled distal end (80) of the needle (10) in order to allow diffusion of the laser light.

At its proximal end, the instrument includes connection means (4) to an optical cable (7) to link the instrument to light from a laser source, which is not represented in FIGS. 2 and 3.

A space (12), forming a channel between needle 10 and fibre 11 can be used to inject an anaesthetic before the laser pulse. This space can also be used to check that the distal end (8) is positioned correctly, with the reflux of blood in the needle acting as the indicator.

The instrument of FIG. 2 provides frontal diffusion of the light that is transmitted substantially on the axis of the optical fibre (12). The bevel at the end of the fibre (12) is used however to laterally shift the diffusion of a part of the light.

Figure 4:
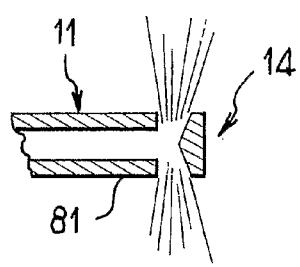
FIG. 4 is a section at one end of a light guide designed for lateral diffusion of the light, in a second embodiment.
Figure 6:
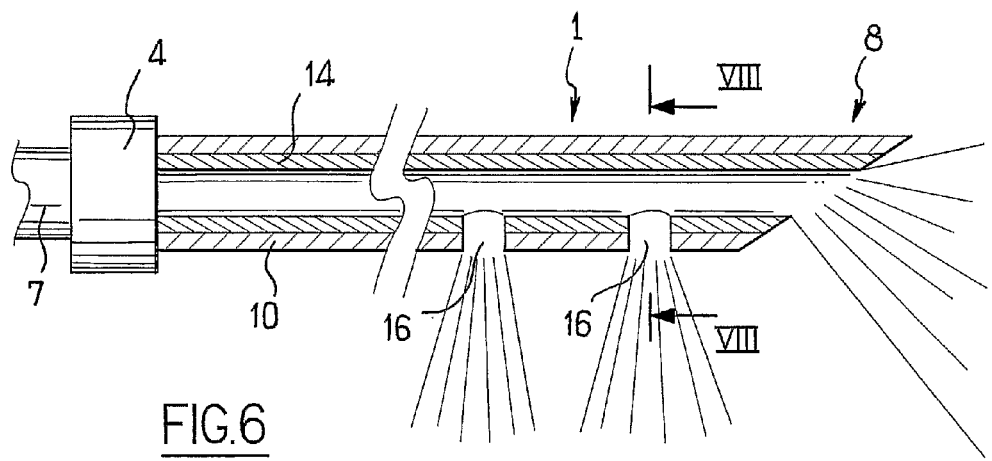
FIG. 6 is a cross section, similar to those of FIGS. 2 and 5, of a third embodiment, in which the light guide is applied to the inner wall of the needle, and in which the diffusion of the light is effected through an axial opening and lateral openings.
Figure 8:
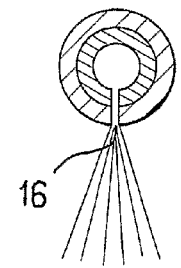
FIG. 8 is a cross section along VIII-VIII of the needle of FIG. 6.

As illustrated in FIG. 4 in a second embodiment, at the distal end (81) of the optical fibre is located lateral diffuser (14) for lateral diffusion of the light. Diffuser 14 enables easier circumferental treatment of the subject. In the example of FIG. 4, lateral diffuser 14 completely stops frontal diffusion of the light. It is also possible to provide diffusers that provide both frontal and lateral diffusion of the light, as illustrated in FIGS. 6 and 8 for example, which are described below.

Figure 7:
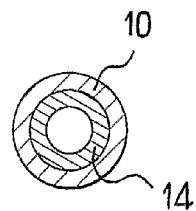
FIG. 7 is a cross section along VII-VII of the needle of FIG. 5.

A third embodiment of an instrument according to preferred embodiments of the invention will now be described with reference to FIGS. 5 and 7, but only insofar as it differs from the embodiment of FIG. 2.

Figure 5:
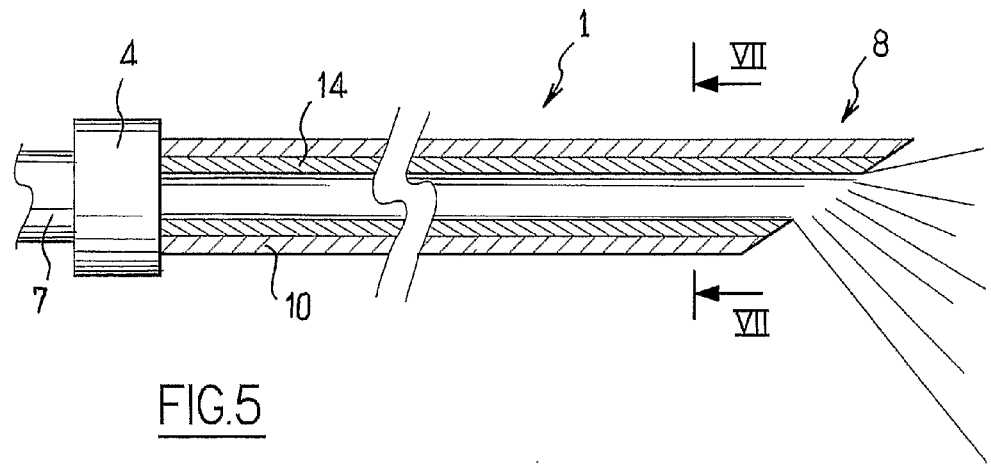
FIG. 5 is a cross section, similar to that of FIG. 2, in a third embodiment, in which the light guide is applied to the inner wall of the needle, and in which the diffusion of the light is effected through an axial opening.

In FIG. 5, the light guide (14) does not include an optical fibre independent of the needle. In FIG. 5, the light guide takes the form of a coating (14) on the interior surface of the needle (10). This coating is attached to the needle over the entire surface thus lined. The coating is in silica, and has the same guidance qualities of the light as an optical fibre. It also has the benefit of protecting the sheath that is afforded by needle (10), in particular in terms of solidity, and of protecting against impact. In addition, since the coating is attached to the needle, the precision of the instrument is increased.

The bevel at the distal end (8) of the instrument affects the needle and its coating in an identical manner, with the distal ends of the light guide and the needle being substantially coincident.

FIGS. 6 and 8 are illustrations of a fourth embodiment, which is a variant of the embodiment of FIG. 5. In this embodiment, as well as the opening allowing a substantially frontal diffusion of the light through the distal end (8), the instrument (1) includes two lateral windows (16). These windows are formed transversally through the wall of the needle and through its coating, away from the distal end (8). The windows are substantially aligned on a generatrix of the cylinder formed by the needle. Such windows allow simultaneous lateral and frontal diffusion of the light. Their location can be chosen in particular to suit the zone to be treated.

Naturally, the invention is not limited to the examples that have just been described, and many changes can be made to these examples without moving outside the scope of the invention.

Thus, in particular for greater precision, it can be advantageous for the light guide, an optical fibre for example, to extend beyond the support, such as a needle for example. The fibre should overshoot the support by 0 to 1 cm, and preferably by about 5 mm. In order to protect the optical fibre during a puncture procedure, a structure can be provided to retract the fibre into the needle as well as a structure to extend the optical fibre beyond the distal end of the needle, to a working position.

A structure can also be provided for rotating the light guide in relation to other parts of the instrument, for example in relation to the support, in particular in the case of a needle containing an optical fibre, or in relation to connection means, in particular in the case of a needle coated internally with silica. These rotatable structures thus allow easier circumferential treatment.

In addition, an instrument according to the preferred embodiments of the invention can be used for other vascular applications, such as sclerosis of varices not only on the lower limbs, but also pelvic or oesophageal varices, haemorrhoids, or vascular sclerosis during surgical operations. It is also possible to use an instrument according to the preferred embodiments of the invention to perform a tissular perforation, or as an alternative to biological adhesives of the cyanoacrylate type, for all intra-vascular embolisation, in particular for the congenital or acquired or veinous fistula, in particular for malformations or haemangioma.

Other applications also exist, in particular for tissue destruction, particularly if great precision is required. Thus, in dermatology, the use of a laser with a wavelength of 980 nm, or at the wavelengths of the Erbiums and Holmiums, around 2 picometres, which are absorbed by water, renders an instrument according to the preferred embodiments of the invention particularly effective, in particular for the treatment of condyloma, warts and other cutaneous lesions. Scarring is of a higher quality than that obtained with other techniques.

In the area of cellular destruction, other applications can also be tissular detersion in contact mode, as applied to ulcers for example. An instrument according to the invention can also be used for destroying tissular intra-hepatic metastases for example, in a more ergonomic and less costly manner than by radiofrequency treatment. Tissue destruction by laser involves tissular absorption of the photons, with secondary conversion into heat. Since this absorption is targeted to certain molecular constituents of the tissue (chromophores), the thermal effect is more specific than another method for heating the tissues, as with radiofrequency methods for example. This specificity allows new applications of lasers, such as dynamic phototherapy the treatment of cancers for example.

The use of a rigid support for the light guide allows more precise use and improved handling qualities. Thus, lesions caused by the treatment are more precise. Biological stimulation improves scarring. Bleeding is reduced, as is the risk of infection, carbonisation involving temperatures of around or above 350° C. or 400° C., corresponding to the tissular incandescence. Postoperative pain is also reduced, in particular in the case of ulcer detersion, since there are fewer post-operative infections. There exists a secondary suppression of inflammation and of algogenic factors at the nerve endings.

Furthermore, parameters can be adjustable, including the wavelength, the emission time and the rest time between each pulse, the fluence, the irradiance, the continuous or pulsed mode (simple or multiple) or in the area of destruction according to the optical diffusion at the end of the light guide.

The light guide can be made from a material other than silica, according to the wavelength of laser.

The invention claimed is:

1. A medical instrument comprising a tubular support in which is disposed a light guide, the light guide comprising a diffusion orifice at a distal end thereof, the light guide being configured for connection to a light source, wherein the instrument allows a lateral diffusion of at least part of the light by:
   the support having a distal bevelled orifice, the light guide having a distal bevelled end, the distal bevelled orifice and the distal bevelled end being arranged to shift the light diffusion toward the side of the bevel; and
   at least one of the support or the light guide having at least one lateral window adjacent the distal end thereof.

2. The instrument according to claim 1, wherein the at least one lateral window is formed at the distal end of the support or light guide.

3. The instrument according to claim 1, wherein the light guide is a coating of an inner wall of the support.

4. The instrument according to claim 1, wherein the light guide is an optical fibre.

5. The instrument according to claim 4, wherein the light guide slides inside the support and is extendible from the distal end of the support by 1 centimetre.

6. The instrument according to claim 1, wherein the light guide is in silica.

7. The instrument according to claim 1, further comprising a rotatable structure for rotating at least one of the light guide or the support.

8. The instrument according to claim 1, further comprising a channel formed in the instrument for injecting a liquid by the support or for allowing reflux of the liquid inside the support.

9. The instrument according to claim 1, further comprising a space formed in the instrument for verifying proper positioning of the instrument.

10. The instrument according to claim 1, wherein the at least one lateral window is transversally disposed along at least one of the light guide or the support.

11. The instrument according to claim 1, wherein the at least one lateral window is longitudinally disposed along at least one of the light guide or the support.

12. A system comprising a medical instrument comprising a tubular support in which is disposed a light guide, and a light source, the light guide comprising a diffusion orifice at a distal end thereof, the light guide being configured for connection to the light source, wherein the instrument allows a lateral diffusion of at least part of the light by:
   the support having a distal bevelled orifice, the light guide having a distal bevelled end, the distal bevelled orifice and the distal bevelled end being arranged to shift the light diffusion toward the side of the bevel; and
   at least one of the support or the light guide having at least one lateral window adjacent the distal end thereof; and
   the light source being configured for interaction with at least one of a vascular element or a cellular element.

13. The system according to claim 12, wherein the laser light source is arranged to generate optical wavelengths between 800 and 980 nm.

14. The system according to claim 12, wherein the light source is a laser light source.

* * * * *